United States Patent [19]

Sundheim et al.

[11] 4,376,437
[45] Mar. 15, 1983

[54] TOPICAL ENVIRONMENTAL DEVICE

[76] Inventors: Benson R. Sundheim, 127 Deertrack La., Irvington-on-Hudson, N.Y. 10533; Richard F. Grady, 42 N. Fullerton Ave.; George C. Brumlik, 154 Upper Mountain Ave., both of Montclair, N.J. 07042

[21] Appl. No.: 58,656

[22] Filed: Jul. 19, 1979

Related U.S. Application Data

[63] Continuation-in-part of Ser. No. 923,281, Jul. 10, 1978, abandoned, which is a continuation of Ser. No. 803,108, Jun. 3, 1977, abandoned, which is a continuation of Ser. No. 700,700, Jun. 29, 1976, abandoned, which is a continuation of Ser. No. 504,600, Sep. 9, 1974, abandoned.

[51] Int. Cl.³ .................... A61H 33/00; A61M 35/00; A61N 1/30
[52] U.S. Cl. .............................. 128/82.1; 128/132 R; 128/207.21; 128/260; 128/402
[58] Field of Search .................. 128/1 R, 1 B, 24.1, 128/82, 82.1, 132 R, 207.19, 207.21, 207.26, 207.27, 248, 254, 256, 260, 299, 300, 325, 334 R, 362, 368, 370, 375, 400, 783, 795, 796, 798, 802, 803

[56] References Cited

U.S. PATENT DOCUMENTS

| 603,815 | 5/1898 | Duke | 128/803 |
|---|---|---|---|
| 753,990 | 3/1904 | Lutje | 128/207.23 |
| 1,251,258 | 12/1917 | Magill | 128/334 R |
| 1,775,442 | 9/1930 | Sarason | 128/370 X |
| 2,493,155 | 1/1950 | McMillan | 128/802 |
| 3,026,874 | 3/1962 | Stevens | 128/260 |
| 3,217,707 | 11/1965 | Werding | 128/299 X |
| 3,227,130 | 1/1966 | Weiskopf | 128/1 R |
| 3,288,140 | 11/1966 | McCarthy | 128/248 |
| 3,441,015 | 4/1969 | Oatman | 128/66 |
| 3,455,299 | 7/1969 | Gerow | 128/66 |
| 3,477,424 | 11/1969 | Tracy | 128/375 X |
| 3,712,298 | 1/1973 | Snowden et al. | 128/299 X |
| 3,874,387 | 4/1975 | Barbieri | 128/325 |

FOREIGN PATENT DOCUMENTS

| 534367 | 1/1955 | Belgium | 128/1 B |
| 547778 | 4/1942 | United Kingdom | 128/1 R |
| 641061 | 8/1950 | United Kingdom | 128/132 R |

Primary Examiner—Lee S. Cohen
Attorney, Agent, or Firm—Sprung, Horn, Kramer & Woods

[57] ABSTRACT

An apparatus for treatment of a human body having an enclosure equipped with an inlet and outlet is described wherein the inlet is in fluid communication with a source of liquid under pressure. A portion of the enclosure is provided with an open treatment zone. Opposite the inlet is an obstacle such as an impeller to create turbulence in the treatment zone.

19 Claims, 16 Drawing Figures

TOPICAL ENVIRONMENTAL DEVICE

This is a continuation-in-part of application Ser. No. 923,281, filed on July 10, 1978 now abandoned, which in turn is a continuation of application Ser. No. 803,108, filed June 3, 1977, now abandoned, which in turn is a continuation of application Ser. No. 700,700, filed June 29, 1976, now abandoned, which in turn is a continuation of application Ser. No. 504,600, filed Sept. 9, 1974, now abandoned.

BACKGROUND

The control of temperature and the control of chemical environment of isolated or whole parts of the human body have wide applications in clinical medicine. The methods which are currently employed are cumbersome, have inadequate control over the heat flow and the rates of cooling and heating. Both the thermal and chemical environment control devices which are presently available have serious limitations in their ability to restrict the treatment to localized areas. Among the devices currently employed are electrical heating blankets and pads, fluid immersion baths, ice packs, and cooling mattresses. All of these devices suffer from the above-mentioned shortcomings.

The intimate and effective control of topical environments is needed in many areas of clinical medicine including the following: arthritis and related muscular-skeletal disorders, treatment of burns and wounds and of generalized skin eruptions. Topical rapid rate cooling of selected areas prior to operation affords greater ease and precision in the performance of the operation process. This rate of change at the cooling, heating and contacting with material is greatly enhanced has the means of producing turbulence a mechanism which posses an important part of this invention. The rapid rate of cooling also inhibits damaging or undesirable metabolic processes and is expected to limit damage in cerebrovascular incidents. It is the purpose of the present invention to provide effective means for the described and needed topical environmental controls.

The present invention provides detailed and predetermined control of physical and chemical properties of localized topical environments including the following: heating, cooling and fluctuation thereof, including rapid changes in rate and in quantities of heat transferred; pressure and vibration control including ultrasonic applications; control of atmospheric conditions including atmospheric composition, humidity and chemical mist concentration; circulating liquid baths and their physical and chemical properties; turbulence forming means which are impellers or obstacles are introduced into the path of the fluid creating a turbulent flow which greatly increases cooling and heating rates, and exchanges of material between the contacted body tissues and the moving fluid chemical medication of the body surfaces and absorption of medication by the said surfaces including electrophoretic means of absorption. Provisions are included for an effective sterilization of the circulating fluids and for the introduction or removal of the components of the said fluids during the operating cycles.

DESCRIPTION OF THE DRAWINGS

FIGS. 3a to 3g are cross-sectional representations of seals that are used to hermetically attach the topical environment enclosures to the desired part of the body 20;

DETAILED DESCRIPTION OF THE DRAWINGS

Figure 1A:
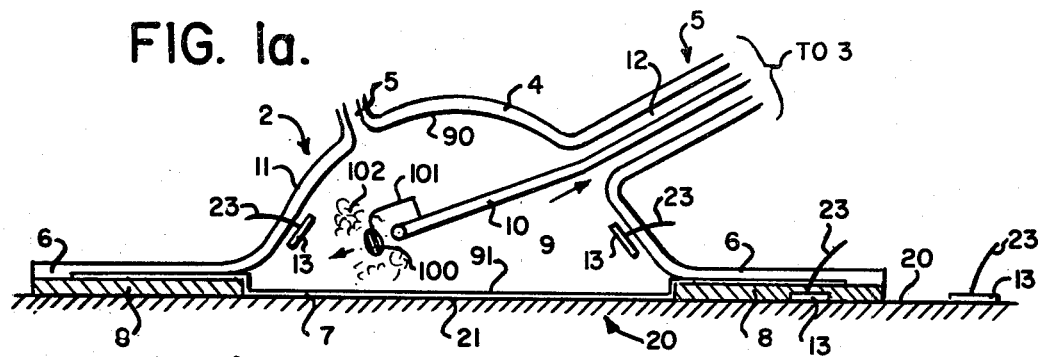
FIG. 1a is a cross-sectional representation of a dome-shaped topical environment enclosure 2 fitted to a surface of a body 20. The dome-shaped enclosure 2 has an inlet 10 and outlet 12 and may be isolated from the said body 20 by a diaphragm membrane 7.
Figure 1B:
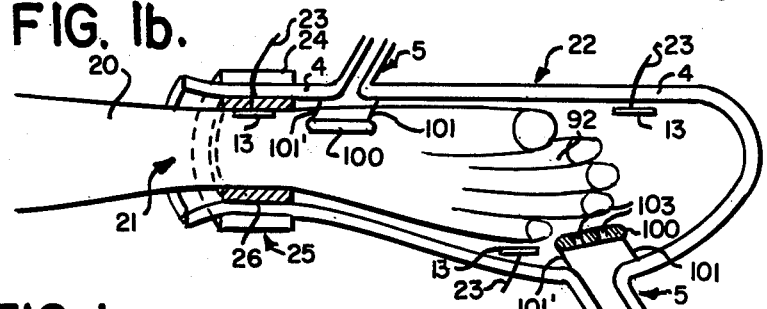
FIG. 1b is a cross-sectional representation of an elongated topical environment enclosure 22 in the form of an elongated bulge whose orifice 21 is equipped with a seal 25.
Figure 1C:
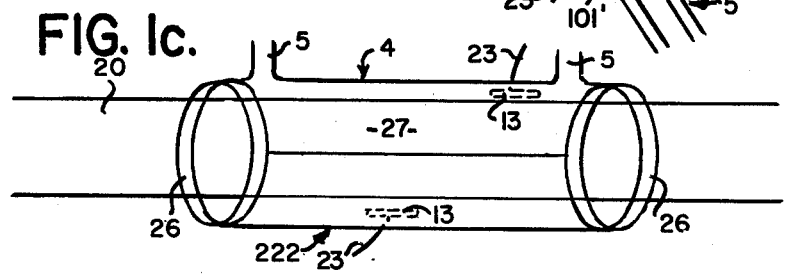
FIG. 1c is a representation of a sleeve-shaped topical environment enclosure open at both ends which are fitted to the body 20 by seals 26.

FIG. 1 is a cross-sectional representation of a dome-shaped topical environmental enclosure 2 having a wall 4 which forms the elevated dome portion 11 equipped with flange 6. The flange 6 is attached to the surface of a body 20 by means of a seal 8 and thus encloses an inner topical environment 9. The seal 8 is further described in connection with FIGS. 3a to 3g and may consist of a reversible permanent adhesive, a pressure sensitive adhesive or may be a mechanical seal. An optional part of the enclosure 2 may be an insulating or permeable membrane 7 which wholly or partially separates the topical environment 9 from the body 20. For purposes of illustration, the dome 2 has been given an oblate shape. Other shapes could be given to the dome without affecting its functionality. For example, the dome 2 may be flat or elongated; it may have a polygonal or polyhedral shape; may have a cylindrical or other symmetry; or may have an irregular shape. The flange 6 may be wide or narrow down to a line and may have any convenient shape. The environmental enclosure 2 may have ports 5 corresponding to an entrance port 10 and an exit port 12 for an exchange or circulation of the inner topical environment 9 accomplished by the topical environmental station 3 shown and described further in connection with FIGS. 4a and 4b. Turbulence forming means such as impellers or obstacles which is positioned for example by a fastening member 101 is held in the path of the moving fluid emerging from the conduit 10 produces turbulence 102 in its flow pattern. Turbulence producing means are shown also in FIGS. 1b, 1c, 2a, 2b, and 2c. The obstacle may be, for example, in a spherical, flat plate, thick or thin, a cyclinder or may be a passive or driven impeller shown in FIGS. 5a to 5c. The topical environment 9 may be comprised of a fluid such as gas, vapor, or a liquid of any desired physical, chemical and/or medicated composition which may be in any desired state of flow, turbulence or vibration. The fluid may serve, for example, as a medium for the propagation electromagnetic and mechanical energy such as, for example, electromagnetic irradiation, ultrasound and other types of energy. The fluid comprising the environment 9 may be present as such or may permeate at least in part a porous retentive medium such as a cellular sponge or a pad composed of a fibrous material. The entrance and exit ports 10 and 12 as shown may be reversed with respect to one another; may enter at one site or at different sites and may be located at any desired locus of the dome. Any number of such ports may be provided and may be represented, for example, by sections of perforated or porous walls which permit an entrance or exit of a fluid from, or to, the inner topical environment 9.

It must be appreciated that by means of a circulating fluid a great control over the topical environment 9 and its neighboring part of the body 20 is achieved. For example, rapid cooling and/or heating of a selected part of the body 20 is effected at such fast rates that cannot be presently obtained. The treated area is accurately localized and isolated from the rest of the body.

The topical environmental enclosure device 2 may be provided with any number of electrodes 13, the said electrodes taking any desired size, shape or form.

Enclosures of the type represented in FIG. 1b are particularly valuable for providing a topical localized environment for the treatment of extremities and appendages of bodies.

Figure 4A:
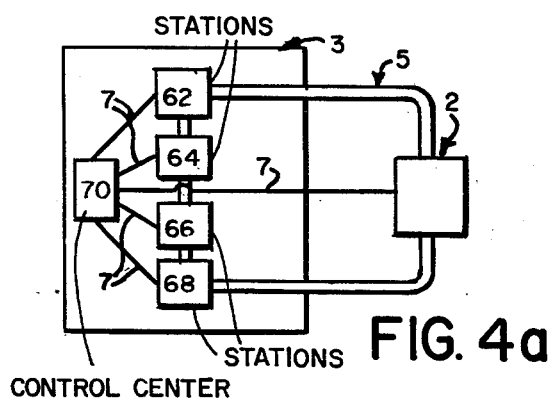
FIGS. 4a and 4b are schematic representations of the logical circuits of the topical environmental devices, including the topical environmental stations 3 whose function is to supply the controlled environment to a selected locus, for example to the topical environment enclosures 2, or their variations 22, or 222.
Figure 4B:
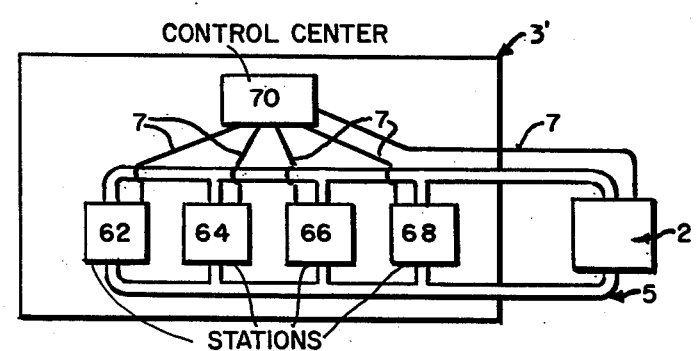

FIG. 1c is a representation in perspective of a sleeve-shaped topical environmental enclosure 222 open at both ends which are attached to the body 20 by means of seals 26 (described in detail in FIG. 1b) so as to enclose a topical environment 9 around the body 20 within the enclosure 222. A turbulence forming means is positioned at port entry 5 and produces turbulence. A provision is included for the introduction of turbulent flow 102 by means of an obstacle 100 which may be attached by means of a support, or supports 101 and 101' as shown in FIGS. 1a, 1b, 2a, 2b, and 2c. The obstacle 100 producing the turbulent flow 102 may have channels 103 within it so as to modify further the turbulent flow 102 as is shown in FIG. 1b. The turbulent flow pattern 102 is of great importance since it contacts turbulently the walls of the isolation container as well as diaphragm 21 overlying the isolated part of the body 20 is shown in FIG. 1a or the skin 90 of the hand 21 as shown in FIG. 1b. The turbulence of the fluid messages the body areas of the topical enclosure, greatly accelerates heating or cooling thereof and rapidly exchanges the access of medication to the isolated areas of the body and removes much faster any waste products therefrom—in comparison to the flow of a fluid that does not possess said turbulence. The enclosure may have an optional separating junction along the line 27 which can be hermetically sealed when closed for example by a hermetically sealing zipper. An environmental fluid provided by the topical environmental station 3, described and illustrated in connection with FIGS. 4a and 4b is circulated through ports 5 of which there may be any suitable number. Numeral 13 represents electrodes equipped with an electrical lead 23 for electrophoretic medication or other electrical treatment of the enclosed topical area. The topical environmental enclosure device 2 may be provided with an number of electrodes 13, the said electrodes taking any desired size, shape or form. The sleeve-shaped topical environmental enclosure 222 is particularly valuable for providing topical local environment for the treatment of portions of the limbs, the neck, and portions of the head and of the torso as well as the treatment of various joints such as ankles, knees, elbows, wrists and knuckles.

Figure 2A:
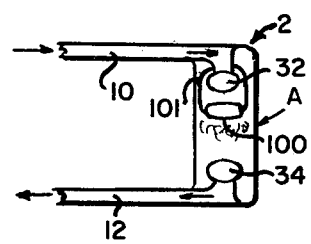
FIGS. 2a, b, and c depict cross-sectional and perspective bodies of parts and of the inlet and outlet tubes systems which connect the topical environment enclosure to the topical environment stations described in FIGS. 4a and 4b.

FIG. 2a is cross-sectional representation of ports, such as the inlet port 10 and exit port 12, both of which terminate at fritted, porous, or perforated walls 32 and 34 respectively within the environmental chamber 2.

Figure 2B:
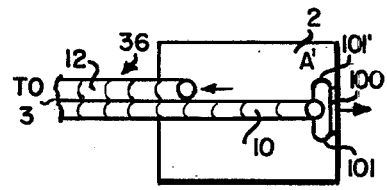

FIG. 2b is a representation in perspective of a flow connector 36 in which a pair of tubes 10 and 12 joined in parallel which may connect the topical environmental station 3 (shown in FIGS. 4a and 4b) with the topical environmental chamber 2. Tube 10 may be the inlet tube and tube 12 may be the outlet tube or vice-versa.

Figure 2C:
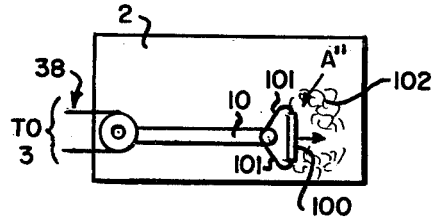

FIG. 2c depicts a perspective view of a flow connector 38 for connecting the topical environmental chamber 2 with the topical environmental stations 3. The connector consists of two coaxial tubes of which the inner tube 10 may provide the entrance port and the outer tube 12 may provide the exit port or the other way. Various shaped turbulence means are depicted in FIGS. 2a, 2b and 2c, spherical A, plate A' and hemispherical A".

Figure 3A:
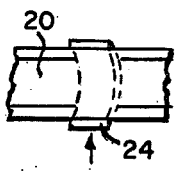
Figure 3B:
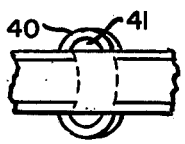
Figure 3C:
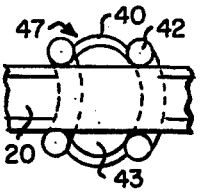
Figure 3D:
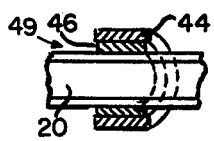
Figure 3D:
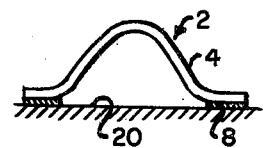

FIGS. 3a to 3g are various cross-sectional views of the seals employed in the present invention. FIG. 3a represents a pressure sleeve 24 which may be a tightened belt, an inflated hollow sleeve, or an inflated belt. FIG. 3b depicts a toroidial seal 40 of a through-like cross-section. The trough contains gas 41 at a reduced pressure which causes the seal to be held tightly against the body 20. FIG. 3c depicts a seal comprising two inflated toroidial hollow compartments 42 located at the sides of a trough 40 which contains a gas under reduced pressure. As in FIG. 3b, the atmospheric pressure tightens the seal 47 against the body 20.

The toroidial seal 49 comprises a sleeve 44 sealed onto the body 20 by means of an adhesive layer 46.

Figure 3F:
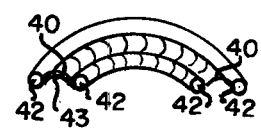

While the FIGS. 3a to 3d represent seals for enclosures surrounding a body, FIGS. 3e and 3f relate to seals for enclosures attached against a face of a body. The dome type enclosure 2 with a wall 4 and a seal 8 represented in cross-section in FIG. 3e may be held against the surface of the body 20 by means of a reversible adhesive, by means of atmospheric pressures which is larger than the reduced pressure 43 inside of the dome, or by means of a special seal represented in FIG. 3f, which is analogous to the seal in FIG. 3c but in FIG. "3f" is depicted flat, rather than cyclindrical as is shown in FIG. 3c.

Figure 3G:
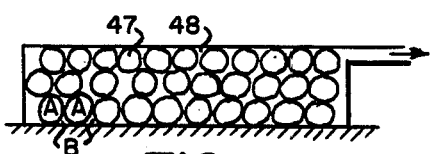

FIG. 3g is a cross-sectional representation of a seal operating by means of reduced pressure within the pores 48 of the seal body which is filled with pressure resisting particles 47 having the pores 48 between them. Such a seal prevents the drawing up of the surface of the body 20 into the seal area, while still operating as a suction cup utilizing atmospheric pressure to effect the seal.

FIGS. 4a and 4b are schematic representations of the topical environmental devices comprising the topical environmental enclosure 2 whose environment is supplied, maintained, cycled and monitored by the topical environmental station 3. The topical environmental station 3 is in turn comprised of one or more substations. These substations may include the following: the circulation station 62; the heat exchange, temperature and pressure control station 64 for cooling and/or heating the circulating environmental fluid 9.

The chemical exchange and medication control station 66 for introduction into and removal from of chemical constituents of the circulating fluid 9, and a sterilization station 68 for the maintenance of sterile conditions in the circulating fluid 9. This means that the described apparatus enables the introduction and removal of medication in a predetermined sequence—a valuable feature not provided by prior art. The periodic provision of medication can also be combined by electophoretic means described in the text. The stations 62, 64, 66 and 68 as well as the topical environmental enclosure device 2 may have their own dependent controls or may be controlled by a central electronic station 70. Numeral 5 represents the circulating conduits through which the fluid 9 is conducted into the elements of the topical environmental device, while numeral 7 represents electrical or information channels for the flow of information and control signals between the active substations 62,64, 66 and 68, the topical environmental enclosure 2; and the controlling center 70.

In FIG. 4a the substations 62, 64, 66 and 68 are arranged in series. Each of the substations, if employed, may have a bypass channel (not shown) and thus may be temporarily or permanently removed from the circuit of flow. In FIG. 4b the substations 62, 64, 66 and 68 are arranged in parallel and can be taken out of the flow circuit by simply interrupting the flow either through the chemical substation 66, the thermal substation 64, or the sterilization station 68. The topical environmental device may consist of all or any of the components of the system as described in connection with FIGS. 4a and 4b and other pertinent parts which are described in the present invention or of any combination thereof.

Figure 5A:
FIG. 5a to c are schematic representations of impellers for producing turbulence in the fluid.
Figure 5B:
Figure 5C:

FIG. 5a is an impeller rotor 80 having two blades 81 and 82 which may be of the same or different size, geometry and pitch. FIG. 5b is a disc rotor 84 with impelling channels 83 which may be slanted and have a cyclindrical or truncated shape. FIG. 5c shows an impeller rotor 88 having a single blade 86.

The topical environmental enclosures of the present invention are particularly valuable in medical application. In addition the topical environmental enclosures together with the topical environmental station can also be employed for chemical and physical treatment of isolated areas of objects so as to bring about transient or permanent physical and/or chemical changes in the desired localized areas of the said objects.

What is claimed is:

1. An apparatus for the treatment of a human body which comprises an enclosure defined by at least one wall, said enclosure adapted to be placed on said body, said enclosure having at least one opening defining an open treating zone adapted to at least partially contain said body, at least one seal attached to said enclosure and disposed about said opening, said seal adapted to seal the contents of said enclosure from the environment outside of said enclosure, an inlet conduit terminating within said enclosure and passing through said wall, a source of liquid disposed outside said enclosure, said inlet conduit being in liquid flow communication with said source of liquid disposed outside said enclosure, means for causing said liquid to flow, under pressure, from said source through said inlet conduit into said enclosure, an impeller disposed within said enclosure, said impeller disposed opposite the terminus of said inlet conduit and in the path of flow of liquid passing through said inlet conduit, said impeller being disposed a distance away from the terminus of said inlet conduit whereby when liquid from said inlet conduit strikes said impeller, said liquid becomes disposed in said enclosure in a state of turbulence and flows towards said open treating zone, said apparatus further comprising an exit conduit from said enclosure.

2. An apparatus according to claim 1, wherein said impeller is attached directly to said inlet conduit.

3. An apparatus according to claim 2, wherein said exit conduit comprises means for withdrawing liquid from within said enclosure and said apparatus comprises means for recirculating said liquid through said inlet conduit.

4. An apparatus according to claim 3, wherein said apparatus further comprises temperature regulation means for regulating the temperature of said liquid as it is recirculated to said inlet conduit.

5. An apparatus according to claim 3, further comprising means for regulating the pressure of said liquid as it is recirculated and passed to said inlet conduit.

6. An apparatus according to claim 3, further comprising means for controlling the material composition of said liquid as it is recirculated.

7. An apparatus according to claim 6, wherein said apparatus further comprises means for sterilizing said liquid as it is recirculated.

8. An apparatus according to claim 2, wherein said seal is an adhesive seal.

9. An apparatus according to claim 2, wherein said seal is a pressure-sensitive seal.

10. An apparatus according to claim 2, wherein said seal is a mechanical pressure seal.

11. An apparatus according to claim 2, wherein said seal is a vacuum seal.

12. An apparatus according to claim 2, wherein said seal comprises a band adaptable to be tightened around a section of a body and to circumscribe said body.

13. An apparatus according to claim 2, wherein said wall comprises a sleeve open at both ends, said sleeve having a seal disposed at each end.

14. An apparatus according to claim 2, wherein said enclosure is in the form of an elongated tube closed at one end and provided with said seal at its open treating zone.

15. An apparatus according to claim 2, wherein said enclosure has a dome shape and said seal is provided at the edges of said dome at the periphery of the base thereof.

16. An apparatus according to claim 2, wherein there is disposed within said enclosure a membrane disposed over said open treating zone.

17. An apparatus according to claim 2, wherein said impeller is a passive impeller.

18. An apparatus according to claim 2, wherein said impeller is a driven impeller and said apparatus comprises means for driving said impeller.

19. An apparatus according to claim 2, wherein said apparatus further comprises a pair of opposed electrodes disposed within the said enclosure and a source of current, said electrodes being in electrical contact with said source of current.

* * * * *